United States Patent [19]

Gray, Sr.

[11] Patent Number: 5,328,448
[45] Date of Patent: Jul. 12, 1994

[54] FINGER JOINT THERAPY APPARATUS

[76] Inventor: Richard O. Gray, Sr., 3625 Saratoga, Downers Grove, Ill. 60515

[21] Appl. No.: 33,258

[22] Filed: Mar. 16, 1993

[51] Int. Cl.⁵ .............. A61F 5/00; A63B 23/16
[52] U.S. Cl. ..................... 602/22; 482/44; 482/47; 601/40
[58] Field of Search ............ 482/44, 47, 48; 602/22; 128/880, 26; 273/54 B; 2/21

[56] References Cited

U.S. PATENT DOCUMENTS

| | | |
|---|---|---|
| 2,357,323 | 9/1944 | Goldberg . |
| 2,520,035 | 8/1950 | Goldberg . |
| 3,011,171 | 12/1961 | Pell . |
| 3,756,222 | 9/1973 | Ketchum . |
| 3,794,019 | 2/1974 | Ritland et al. . |
| 3,937,215 | 2/1976 | Barthlome . |
| 4,220,334 | 9/1980 | Kanamoto et al. . |
| 4,274,399 | 6/1981 | Mummert . |
| 4,368,728 | 1/1983 | Pasbrig . |
| 4,456,002 | 6/1984 | Barber et al. . |
| 4,677,971 | 7/1987 | Lindemann ............ 273/54 B |
| 4,679,548 | 7/1987 | Pecheux . |
| 4,772,012 | 9/1988 | Chesher . |
| 4,945,902 | 8/1990 | Dorer et al. . |

Primary Examiner—Richard J. Apley
Assistant Examiner—Lynne A. Reichard
Attorney, Agent, or Firm—Richard O. Gray, Jr.

[57] ABSTRACT

An apparatus treats a stiffened joint of at least one finger of the hand and includes a first member for engaging the metacarpal phalangeal joint of the finger and a second member movable with respect to the first member for engaging a surface of the finger on the side of the stiffened joint opposite the metacarpal phalangeal joint. The apparatus further includes at least one threaded member for exerting pressure against the second member for bending the stiffened joint and retaining the apparatus on the hand.

12 Claims, 2 Drawing Sheets

FINGER JOINT THERAPY APPARATUS

BACKGROUND OF THE INVENTION

The present invention is generally directed to a finger joint therapy apparatus for restoring flexibility to the finger joints of the hand. The present invention is more particularly directed to such an apparatus which provides flexibility therapy to the metacarpal phalangeal (MCP) joints, the proximal interphalangeal (PIP) joints, or the distal interphalangeal (DIP) joints of the hand.

Following hand surgery or other trauma to the hand, finger joints of the hand often become stiffened and will not bend to their fullest extent. In such cases, finger joint therapy is generally indicated.

In the prior art, such finger joint therapy has been carried out through the use of customized orthotic devices. One such device fits the palm of the hand and is made of plastic. The plastic is configured to roll up the sides and partially the back of the hand. To provide restraint, the plastic may further roll up the thumb to some extent. For the finger to be treated, the plastic further rolls up that finger to restrain the first knuckle or MCP joint from bending. A hook is then glued onto the fingernail of the finger to be treated and another hook is glued to the plastic device. A rubber band is then extended between the two hooks to apply bending pressure to the PIP and DIP joints. Typically, the device is used in this manner to provide therapy to the afflicted stiffened joints for five minutes of each awakened hour.

Such devices exhibit a number of disadvantages. First, they are relatively expensive due to their customization. Secondly, they are difficult to use given the many steps required for proper positioning on the hand and the connection of the rubber band between the hooks. Third, they are inconvenient, especially due to the fact that the therapy patient must live with a hook glued to the fingernail of the finger under therapy for perhaps a matter of weeks. Lastly, such devices do not provide adequate therapy for afflicted MCP joints.

There is therefore a need in the art for a new and improved finger joint therapy apparatus. Such an apparatus should be convenient to use and be adjustable to accommodate hands of different sizes. This would both negate the need for a customized device and greatly reduce the concomitant expense of such devices. Additionally, such a device preferably would eliminate the need for hooks glued to a patient's fingernail. Lastly, such a device should further preferably conveniently fit onto a patient's hand, thereby giving the patient greater freedom of movement during therapy. Further, there is a need in the art for such a device which conveniently treats the MCP joints of the hand. The apparatus of the present invention provides solutions to all of the above-noted disadvantages in the prior art.

SUMMARY OF THE INVENTION

The present invention provides an apparatus for treating a stiffened joint of at least one finger of the hand. The apparatus includes a first member for engaging the metacarpal phalangeal joint of the finger and a second member movable with respect to the first member for engaging a surface of the finger on the side of the stiffened joint opposite the metacarpal phalangeal joint. The apparatus further includes pressure means for exerting pressure against the second member for bending the stiffened joint and retaining the apparatus on the hand.

In accordance with one aspect of the present invention, the first member includes an inwardly-turned first end for engaging the metacarpal phalangeal joint of the finger and an extension for extending along the finger between the metacarpal phalangeal joint and the proximal interphalangeal joint of the finger. The first member may further include a second end opposite the first end and wherein the apparatus further includes a third member having a first end coupled to the second end of the first member with the third member extending inwardly from the second end of the first member and forming an angle with the extension of the first member for inwardly bending the proximal interphalangeal joint and confining the proximal interphalangeal joint of the finger between the extension of the first member and the third member. In accordance with a further aspect of the present invention, the second member may extend from the third member for engaging the finger between the distal interphalangeal joint and the tip of the finger for inwardly bending the distal interphalangeal joint of the finger.

In accordance with a further aspect of the present invention, the apparatus may further include a third member spaced from the first member and extending substantially co-extensively to the first member to form a space through which the fingers of the hand may extend for engaging the first member with the top surface of the hand proximal to the metacarpal phalangeal joint of each finger of the hand and for engaging the third member with the bottom surface of the hand proximal to the metacarpal phalangeal joint of each finger of the hand. The second member is preferably arranged to engage the top surface of the at least one finger on the side of the metacarpal phalangeal joint opposite the first and third members and the pressure means preferably exerts pressure against the second member for inwardly bending the metacarpal phalangeal joint of the at least one finger. In accordance with a further aspect of the present invention, a fourth member may extend from the first member and carries the pressure means which is coupled to the second member. In accordance with further aspects of the present invention, a plurality of the fourth members, a like plurality of the pressure means, and a like plurality of the second members may be provided on the first member for simultaneously treating a like plurality of metacarpal phalangeal joints of the hand.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify identical elements, and wherein:

DESCRIPTION OF THE PREFERRED EMBODIMENTS

Figure 1:
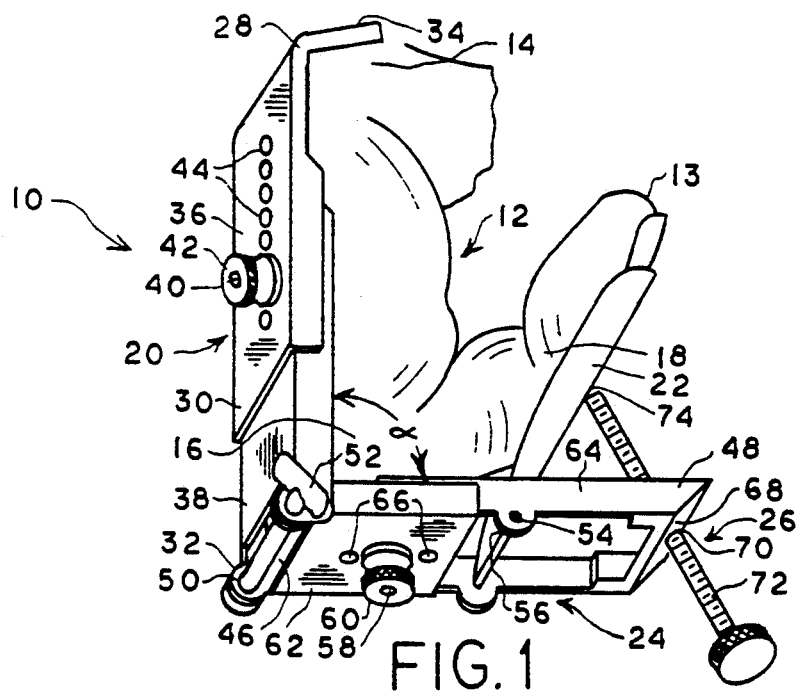
FIG. 1 is a perspective view of a finger joint therapy apparatus structured in accordance with a first embodiment of the present invention shown in conjunction with a human finger undergoing therapy.

Referring now to FIG. 1, it illustrates a finger joint therapy apparatus 10 structured in accordance with a first preferred embodiment of the present invention shown in conjunction with a finger 12 under therapy. The various joints of the finger to be referred to hereinafter are the metacarpal phalangeal (MCP) joint 14, commonly referred to as the knuckle, the proximal interphalangeal (PIP) joint 16, commonly referred to as the middle joint of the finger, and the distal interphalangeal (DIP) joint 18. As will be seen hereinafter, the apparatus 10 is particularly adapted for providing flexibility therapy to the PIP joint 16 and the DIP joint 18.

The apparatus 10 generally includes a first member 20, a second member 22, and a third member 24. The apparatus further generally includes a pressure exerting means 26.

The first member 20 includes a first end 28, an extension 30, and a second end 32. The first end 28 includes an inwardly-turned portion 34 which is arranged to engage the metacarpal phalangeal joint 14 of the finger 12. The extension 30 includes a first extension component 36 and a second extension component 38. Extension component 38 carries a threaded screw 40 which is arranged to threadingly receive a knurled nut 42. The first extension component 36 includes a plurality of apertures 44 which, together with the screw 40 and knurled nut 42, form an adjustment means for adjusting the longitudinal length of the first member 20. As can be noted from the figure, the knurled nut 42 may be removed and the threaded screw 40 placed through a desired one of the apertures 44 to adjust the longitudinal length of the first member 20. Preferably, the longitudinal length of the first member 20 is selected so that the extension 30 extends between the PIP joint 16 and the MCP joint 14 as illustrated. Once the proper aperture has been selected, the knurled nut 42 may be threadingly engaged with the threaded screw 40 to maintain the proper longitudinal length of the first member 20.

The third member 24 includes a first end 46 and a second end 48. The first end 46 of the third member 24 is hingedly coupled to the second end 32 of the first member 20 by a hinge means 50. A retaining means in the form of a wing screw 52 is provided for maintaining the first member 20 and the third member 24 in a preselected fixed angular disposition. As will be noted from FIG. 1, the first member 20 and third member 24 are hingedly coupled together to form an angle α therebetween for confining the PIP joint 16 between the extension 30 and the third member 24 and for bending the PIP. joint.

The second member 22 is connected to the third member 24 at a coupling point 54 by a pivot means 56 for pivotally connecting the second member 22 to the third member 24. The second member extends from the third member 24 to engage the finger 12 between the DIP joint 18 and the tip 13 of the finger.

The third member 24 also includes an adjustment means in the form of a threaded screw 58 and a knurled nut 60 in a manner similar to the first member 20. The third member 24 is formed by a first section 62 and a second section 64. The second section 64 carries the threaded screw 58 which may be extended through any one of a plurality of apertures 66 in the first section 62 to adjust the distance between the first end 46 of the third member 24 and the coupling point 54. Once the proper aperture 66 has been selected, the knurled nut 60 may be tightened on the threaded screw 58 to maintain the properly selected distance.

The second end 48 of the third member 24 carries the pressure exerting means 26. The third member 24 includes a rear wall 68 having a threaded aperture 70. The threaded aperture 70 threadingly receives a threaded member 72 of the pressure exerting means 26. The threaded member 72 includes an engaging end 74 which engages the second member 22. As can thus be noted in FIG. 1, when the threaded member 72 is turned within the threaded aperture 70, pressure is exerted against the second member 22 to cause inward bending of the DIP joint 18 of the finger 12.

In use of the apparatus 10, the threaded member 72 is loosened to permit the finger 12 to be inserted into the apparatus 10 as illustrated. For purposes of this discussion, it is assumed that the longitudinal length of the first member 20 and the distance between the hinged coupling of the first member 20 and the second member 24 and the coupling point 54 have been previously selected. The finger 12 is then inserted into the apparatus as illustrated with the PIP joint 16 being confined between the extension 30 of the first member 20 and the third member 24. The threaded member 72 is then threadingly turned within the aperture 70 to force the second member 22 in a counterclockwise direction in engagement with the finger 12 between the PIP joint 18 and the tip 13 of the finger 12. The finger tip 13 and joint 18 will ride up the ramp provided by the inside of member 22 bending joints 16 and 18. The threaded member 72 is tightened until some pain, stretch, is felt in the finger. When the pain, stretch, in the finger subsides, the threaded member 72 may be turned further until the desired amount of pressure is exerted against the finger by the second member 22.

If desired, to provide greater comfort, the inner surfaces of the first member 20, the second member 22, and the third member 24 may be lined with felt, rubber, or other suitable soft material. The therapy thus provided to the finger 12 is preferably continued for five minutes during each awakened hour of the day. As will be noted from FIG. 1, the first member 20 by virtue of the inwardly turned portion 34 engaging the MCP joint and the second member 22 engaging the finger as illustrated provides bending therapy to the PIP and DIP joints and further retains the apparatus 10 on the patient's finger 12.

Figure 2:
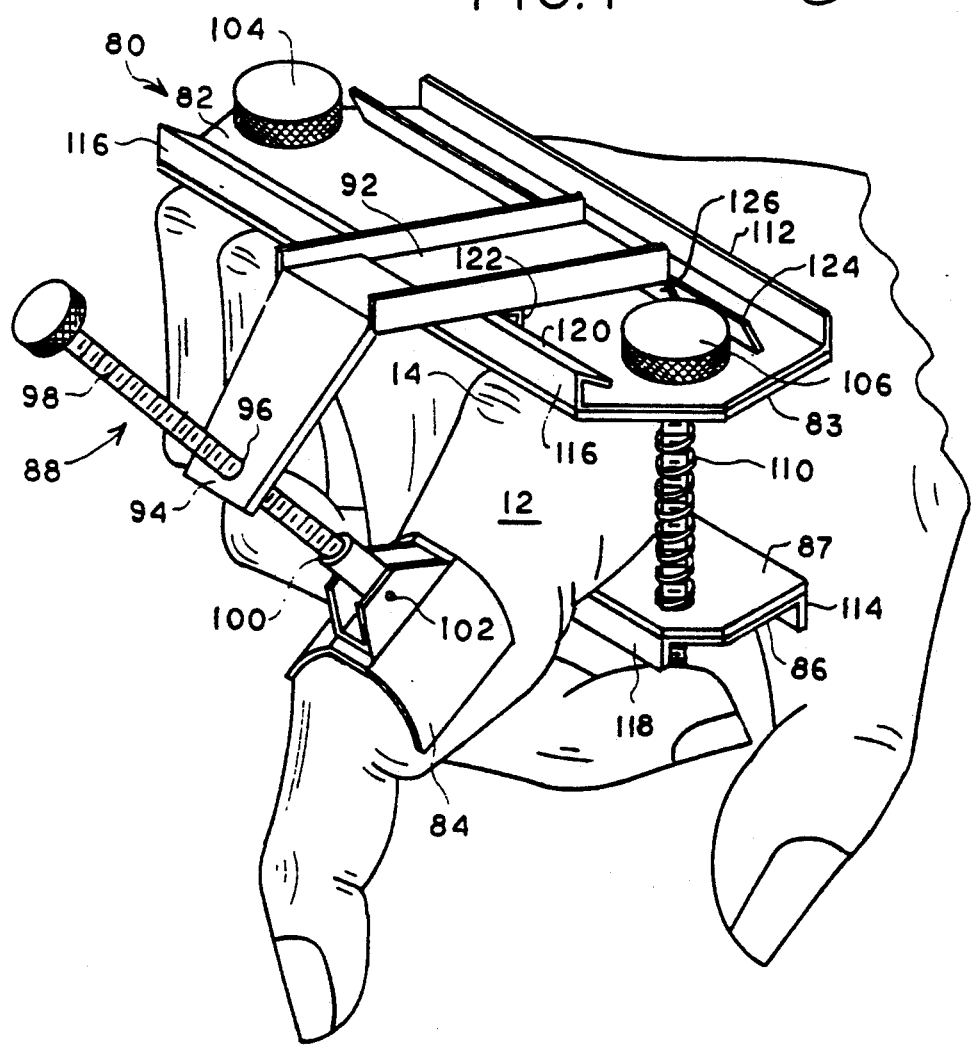
FIG. 2 is a perspective view of a finger joint therapy apparatus structured in accordance with a second preferred embodiment of the present invention shown in conjunction with a human hand, a finger of which being under therapy.
Figure 3:
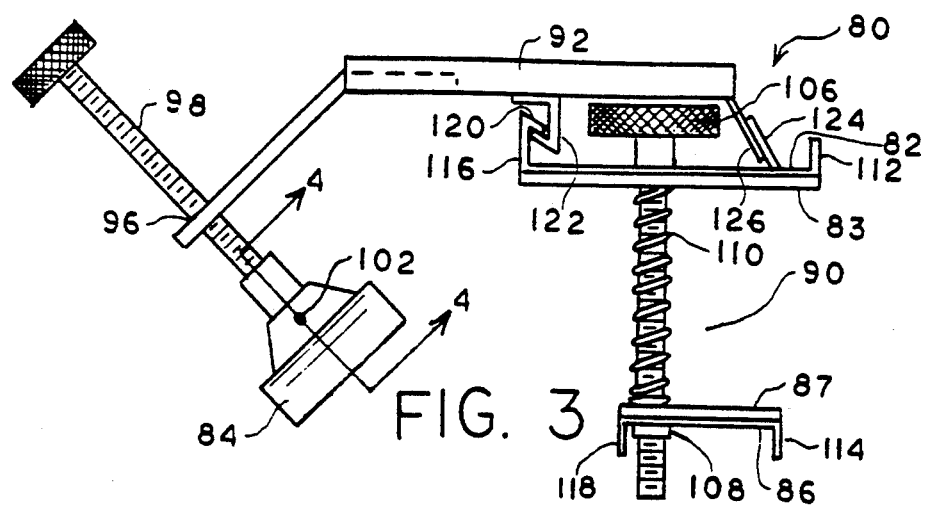
FIG. 3 is a side plan view of the apparatus of FIG. 2.

Referring now to FIGS. 2 and 3, these figures illustrate another finger joint therapy apparatus 80 embodying the present invention. As will be seen hereinafter, the apparatus 80 is particularly adapted for treating the MCP joints of the hand.

The apparatus 80 generally includes a first member 82, a second member 84, a third member 86, and a force exerting means 88. The first member 82 and the third member 86 are spaced apart and extend substantially co-extensively to form a space 90 through which the fingers of the hand may extend to permit the first member 82 to engage the top surface of the hand proximal to the MCP joints of each finger of the hand and the third member 86 to engage the bottom surface of the hand proximal to the MCP joint of each finger of the hand as illustrated. For comfort and to promote better adhesion to the skin of the hand, the inner surfaces of members 82 and 86 are provided with rubber linings 83 and 87 respectively. The second member 84 engages the top surface of the finger 12 under therapy on the side of the MCP joint 14 opposite the first and third members 82 and 86. The pressure exerting means 88 exerts pressure against the second member 84 for inwardly bending the MCP joint 14 of the finger 12 to render therapy to the MCP joint 14.

The pressure exerting means 88 is carried by a fourth member 92. The fourth member 92 extends from the first member 82 and has a distal end 94 which includes a threaded aperture 96.

The pressure exerting means includes a threaded member 98 which is threadingly received by the threaded aperture 96. The threaded member 98 also has an engaging end 100 which is pivotally connected to the second member 84 at a pivot point 102. As the threaded member 98 is turned within the threaded aperture 96, it exerts an increasing pressure against the second member 84 to cause the second member 84 to bend the MCP joint 14 as illustrated.

As may best be seen in FIG. 3, the spacing between the first member 82 and the third member 86 is defined by a pair of screws 104 and 106 which are threadingly received by a pair of embossed threaded portions beneath the third member 86. One such threaded portion 108 is illustrated in FIG. 3 for threadingly receiving the screw 106. By virtue of the screws 104 and 106 and the threaded portions beneath the third member, the separation between the first and third members 82 and 86 defining the space 90 through which the fingers may extend is defined. Preferably, a biasing means in the form of a spring 110 is provided on the screws 104 and 106 between the first member 82 and the third member 86 to maintain the desired separation of the first and third members when the apparatus is not in use.

As will also be noted in FIGS. 2 and 3, the first member 82 is provided with a rear flange 112 and the third member 86 is provided with a rear flange 114 to lend greater rigidity to the first and third members 82 and 86. The first and third members 82 and 86 further include forward flanges 116 and 118 for the same purpose.

The flange 116 also includes a downturned portion 120 for engaging a complementarily-shaped guide flange 122 projecting from the bottom surface of the fourth member 92. The third member 82 further includes an upturned guide flange 124 which engages a downturned guide flange 126 of the fourth member 92. By virtue of the guide flanges 120, 122, 124, and 126, the fourth member 92 may be moved longitudinally along the first member 82 to align the second member 84 with any one of the fingers of the hand. As a result, any one of the MCP joints of the hand may be treated by the apparatus 80.

Figure 4:
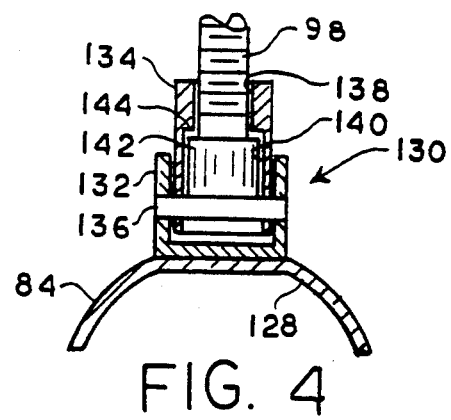
FIG. 4 is a cross-sectional view taken along lines 4—4 of FIG. 3.

FIG. 4 illustrates the manner in which the threaded member 98 is pivotally connected to the second member 84. Firstly, it may be observed from FIG. 4, that the second member 84 includes a concave inner surface 128, which for comfort, may be lined with rubber, felt, or other suitable soft material. This concave inner surface 128 is formed to generally conform to the contour of the finger 12. This of course lends stability to the second member 84 in its engagement with the finger 12 and lends to greater comfort.

The pivotal connection between the threaded member 98 and the second member 84 is provided by a universal joint 130. The universal joint 130 includes a U-shaped bracket carried by the second member 84 which is dimensioned to receive a cylindrically-shaped sleeve 134. The walls of the bracket 132 and the sleeve 134 include aligned apertures through which a pin 136 is received to provide the pivotal connection between the threaded member 98 and the second member 84. The sleeve 134 includes a first bore 138 for loosely receiving the threaded member 98 and a larger bore 140. The threaded member carries a larger diameter end portion 142 which is received within the bore 140. The bore 140 together with the bore 138 forms a shoulder 144 which restrains axial movement of the threaded member 98 from the sleeve 134. As a result, the threaded member 98 is not only pivotally connected to the second member 84, but in addition, is free to be turned within the threaded aperture 96 of the fourth member 92 so as to exert the aforementioned pressure against the second member 84.

Figure 5:
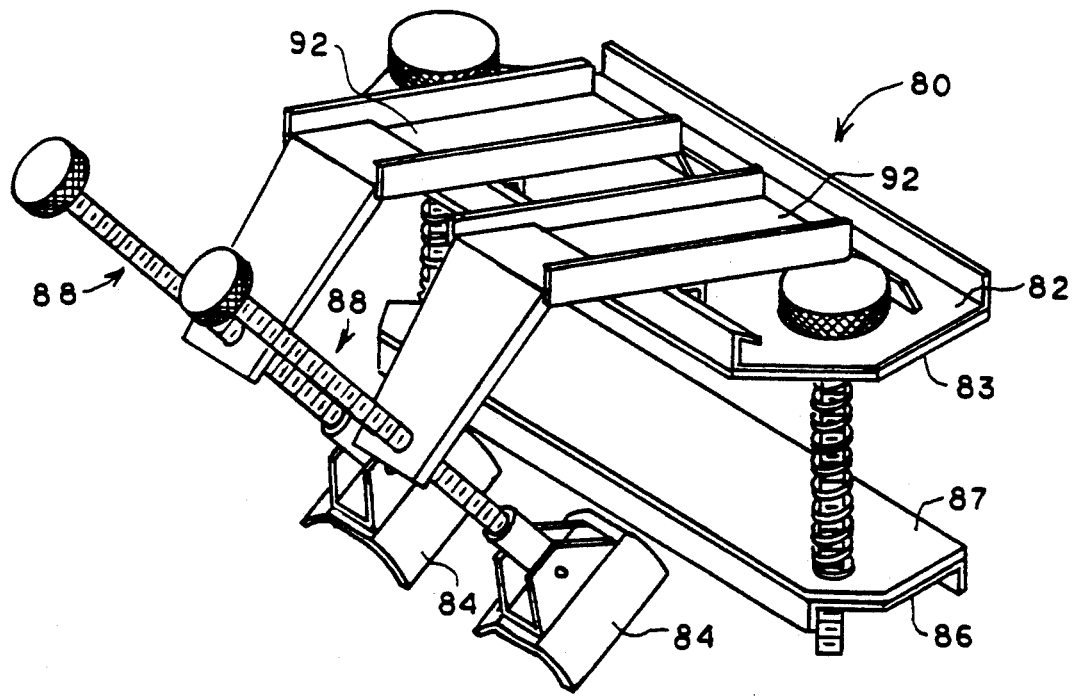
FIG. 5 is a perspective view of the apparatus of FIG. 2 illustrating the manner in which a plurality of fingers may be simultaneously treated with the apparatus of FIG. 2.

Referring now to FIG. 5, it illustrates in perspective view the apparatus 80 of FIG. 2 as it may be further configured in accordance with further aspects of the present invention. As will be noted in FIG. 5, the apparatus 80 includes a plurality of the fourth members and a like plurality of the second members 84 and a like plurality of the pressure exerting means 88. As a result, a plurality of MCP joints of the hand may be simultaneously provided with therapy by the apparatus 80. While two such MCP joints may be provided with therapy by the apparatus 80 illustrated in FIG. 5, it will be appreciated by those skilled in the art that up to all four of the MCP joints of the hand may be simultaneously provided with therapy in accordance with this aspect of the present invention.

As can be seen from the foregoing, the present invention provides a new and improved finger joint therapy apparatus. The apparatus of the present invention is convenient to use and is adjustable to fit any size of hand. In addition, the apparatus of the present invention may be carried entirely by the hand of the patient to thereby render greater freedom of movement to the patient during therapy. Furthermore, the apparatus of the present invention conveniently provides therapy to the DIP, PIP, and MCP joints of the hand. As a result, by virtue of the present invention, patients suffering from trauma to the hand resulting in stiffened finger joints may be provided with more effective and convenient therapy than heretofore possible.

While particular embodiments of the present invention have been shown and described, modifications may be made, and it is therefore intended to cover in the appended claims all such changes and modifications which fall within the true spirit and scope of the invention.

What is claimed is:

1. An apparatus for bending the proximal interphalangeal and distal interphalangeal joints of a finger of a human hand, said apparatus comprising:
   a first member having a turned end portion for engaging the metacarpal phalangeal joint of the finger;
   a second member movable with respect to said first member for engaging a surface of the finger between the distal interphalangeal joint and the tip of the finger; and
   pressure means for exerting pressure against said second member to cause said second member to move toward said first member for bending the proximal interphalangeal and distal interphalangeal joints of the finger between said first and second members, and causing said turned end portion and said second member to retain said apparatus on the hand.

2. An apparatus as defined in claim 1 wherein said first member includes a first end including said turned end portion for engaging the metacarpal phalangeal joint of the finger and an extension for extending along the finger between the metacarpal phalangeal joint and the proximal interphalangeal joint of the finger.

3. An apparatus as defined in claim 2 wherein said first member further includes a second end opposite said first end and wherein said apparatus further includes a third member, said third member having a first end coupled to said second end of said first member, said third member extending from said second end of said first member and forming an angle with said extension of said first member for confining the proximal interphalangeal joint of the finger between said extension of said first member and said third member.

4. An apparatus as defined in claim 3 wherein said apparatus further includes hinge means for hingedly coupling said first end of said third member to said second end of said first member and retaining means for maintaining said angle between said extension and said third member.

5. An apparatus as defined in claim 3 wherein said third member includes a second end and wherein said second member extends from said third member at a coupling point between said first and second ends of said third member.

6. An apparatus as defined in claim 5 further including pivot means for pivotally coupling said second member to said third member at said coupling point.

7. An apparatus as defined in claim 6 wherein said second end of said third member includes said pressure means for exerting said pressure against said second member.

8. An apparatus as defined in claim 7 wherein said pressure means includes threaded means having an engaging end and wherein said third member second end includes a threaded aperture for threadingly receiving said threaded means, said threaded means engaging end for engaging said second member and exerting said pressure against said second member.

9. An apparatus as defined in claim 2 wherein said extension of said first member includes adjustment means for adjusting the longitudinal length of said first member.

10. An apparatus as defined in claim 5 wherein said third member includes adjustment means intermediate said third member first end and said coupling point for adjusting the distance between said third member first end and said coupling point.

11. An apparatus for bending the proximal interphalangeal and the distal interphalangeal joints of a finger of a human hand, said apparatus comprising:
a first member having a first end for engaging the metacarpal phalangeal joint of the finger, said first member also having a second end;
a third member extending from said first member second end for confining the proximal interphalangeal joint of the finger between said first and third members;
a second member pivotally coupled to and extending from said third member and movable with respect to said first member for engaging the finger between the distal interphalangeal joint and tip of the finger; and
pressure means for exerting pressure against said second member and causing said second member to pivot toward said first member for bending the proximal interphalangeal and distal interphalangeal joints of the finger.

12. An apparatus for bending the proximal interphalangeal and the distal interphalangeal joints of a finger of a human hand, said apparatus comprising:
a first member having a turned first end for engaging the metacarpal phalangeal joint of the finger, an extension for extending along the finger between the metacarpal phalangeal joint and the proximal interphalangeal joint of the finger, and a second end;
a third member having a first end coupled to said second end of said first member and extending from said second end of said first member and forming an angle with said extension of said first member for confining the proximal interphalangeal joint of the finger between said extension of said first member and said third member;
hinge means for hingedly coupling said first end of said third member to said second end of said first member;
retaining means for maintaining said angle between said extension and said third member;
a second member extending from said third member and movable with respect to said first member for engaging a surface of the finger between the distal interphalangeal joint and the tip of the finger; and
pressure means for exerting pressure against said second member to cause said second member to move toward said first member for bending the proximal interphalangeal and distal interphalangeal joints of the finger between said first and second members and causing said turned first end and said second member to retain said apparatus on the hand.

* * * * *